United States Patent [19]
Lillwitz

[11] 4,089,871
[45] May 16, 1978

[54] MANUFACTURE OF FURFURYL ALCOHOL
[75] Inventor: Larry D. Lillwitz, Crystal Lake, Ill.
[73] Assignee: The Quaker Oats Company, Chicago, Ill.
[21] Appl. No.: 792,890
[22] Filed: May 2, 1977
[51] Int. Cl.² .................................................. C07D 307/44
[52] U.S. Cl. .................................................. 260/347.8
[58] Field of Search ...................................... 260/347.8
[56] References Cited
U.S. PATENT DOCUMENTS

| | | | |
|---|---|---|---|
| 2,750,394 | 6/1956 | Peniston | 260/347.8 |
| 3,071,599 | 1/1963 | Hales et al. | 260/347.8 |

OTHER PUBLICATIONS

Introduction to the Chemistry of the Furans, Bulletin 202, The Quaker Oats Co. (1947).

Primary Examiner—Richard L. Raymond
Attorney, Agent, or Firm—Joseph P. O'Halloran

[57] ABSTRACT

Furfuryl alcohol is produced by a liquid phase process in which hydroxymethylfurfural is decarbonylated at a temperature at or above 135° C. in the presence of a palladium or rhodium catalyst and in which the furfuryl alcohol is continuously stripped from the reaction medium.

8 Claims, No Drawings

4,089,871

MANUFACTURE OF FURFURYL ALCOHOL

BACKGROUND OF THE INVENTION

Furfuryl alcohol is a highly reactive liquid which has proven to be of widespread commercial value, particularly in connection with adhesives, binders, and other polymeric materials made therefrom. Furfuryl alcohol is highly reactive. Its propensity for exothermic polymerization in the presence of acid catalyst is particularly well known.

Historically the production of furfuryl alcohol has been achieved through the hydrogenation of furfural. (See U.S. Pat. Nos. 2,754,304 and 2,754,307 to Swadesh). Furfural, of course, has been traditionally produced through the acid treatment of agricultural waste material having pentosans contained therein.

Hydroxymethylfurfural can be produced by known methods from hexoses such as glucose or fructose.

An object of the present invention is to provide an alternative route for the manufacture of furfuryl alcohol, which route does not require the presence of pentosan-containing material upstream in the process.

Another object of the present invention is to produce furfuryl alcohol in a process sequence in which a hexose or a cellulosic material is utilized rather than pentoses or pentosans.

SUMMARY OF THE INVENTION

In accordance with the present invention, furfuryl alcohol is produced by contacting hydroxymethylfurfural in the liquid phase with a catalyst selected from the group palladium and rhodium, and continuously removing furfuryl alcohol from the contacting mixture, which process takes place at or above 135° C. In a preferred embodiment, the contacting temperature is at or above the boiling point of furfuryl alcohol at the contacting pressure. It is also essential that the hydroxymethylfurfural ingredient have a pH in the range 6.5 to 9.0 inclusive.

The palladium or rhodium catalyst used in the process of this invention is preferrably supported on one of the many supports known in the art, but it can be provided in a form which is soluble in the reaction medium. Generally speaking, the amount of palladium supported on the carrier is not critical. While a catalyst containing between about 1 percent and 5 percent by weight palladium (expressed as palladium metal) is preferred, catalysts containing considerably more or less palladium or rhodium are eminently satisfactory. The method by which palladium or rhodium catalysts are made are many and varied, and are well known in the art. Any of these methods which result in non-acidic catalysts may be used to prepare the catalyst used in the present invention. For example, the palladium catalyst prepared by the techniques reported in H. E. Eschinazi (Bulletin de la Societe Chemique, 5th Series, Volume 19, Pages 967–969), also in U.S. Pat. No. 3,257,417 to Andrew P. Dunlop and George W. Huffman give good results. The Eschinazi technique involves precipitation of palladium on a support in the form of compounds such as palladium oxide or hydroxide by the addition of sodium carbonate to an aqueous palladium salt. Such a deposit of palladium compounds is converted to palladium metal on contact with the reactants in the process of this invention.

Unsupported and supported palladium or rhodium compounds may also be reduced to metal by any of the well known procedures employed for this purpose.

In addition, palladium catalysts can be provided in a soluble form in accordance with the present invention, such as, for example, in the form of palladium acetate. Palladium acetate is soluble in hydroxymethylfurfural under the conditions of the reaction, and the soluble palladium catalyst did not appear to be converted to palladium metal in such instances and yet functioned well in accordance with this invention.

Suitable catalyst supports include alumina, silica, carbon, barium sulphate, calcium sulphate, diatomaceous earth, etc. It is well known in the art that hydroxymethylfurfural is far more susceptible to polymerization, under both acidic and alkaline conditions, than furfural. Again, the furfuryl alcohol product of the present invention is highly reactive, having great propensity for exothermic polymerization in the presence of small amounts of acid. Hence, the use of a support of palladium catalyst which is acidic, and the use of hydroxymethylfurfural containing acidic impurities, must be avoided in the method of the present invention.

The hydroxymethylfurfural employed in accordance with the present invention should be relatively pure but may be wet. For example, the present invention has worked very successfully in respective runs using hydroxymethylfurfural containing 1, 1.5, and 5 percent water by weight respectively. Hydroxymethylfurfural can be purified by any of the well known procedures used for this purpose to provide the feed for the process of the present invention. In a preferred embodiment, for example, crude hydroxymethylfurfural is treated with aqueous sodium carbonate, and washed until it exhibits a pH in the range 6.5 to 9.0 and the resulting crude hydroxymethylfurfural is fractionally distilled in a wipe film still. The distillate has a pH in the range 6.5 to 9.0. pH can be determined for this purpose by dissolving 1 gram of the ingredient in 10 ml. of water and determining the ph of the solution using conventional equipment.

In accordance with a preferred embodiment of the present invention the contacting of the hydroxymethylfurfural with palladium catalyst takes place in the presence of an alkali metal salt, or an alkaline earth metal salt. In two otherwise identical runs, in accordance with the present invention, in which a so-called "homogeneous" catalyst (palladium acetate) is used, a production run using calcium acetate as an additive gave a productivity rate of 500 grams of furfuryl alcohol per gram of palladium per hour, whereas an otherwise identical run with palladium acetate catalyst (no calcium acetate added) gave a productivity rate of 98.

While the pressure is not critical, in preferred embodiments in which the furfuryl alcohol product is stripped from the reaction medium by vaporization as it is formed, the temperature pressure relationship above the liquid contacting phase must be such that the furfuryl alcohol is removed by vaporization from the contacting phase as soon as it is formed. Hence, temperatures at or above the boiling point of furfuryl alcohol at the pressure encountered, are employed as the contacting temperatures in such embodiments.

Generally speaking, in such embodiments it is preferable to contact the hydroxymethylfurfural and the catalyst at a low pressure even subatmospheric pressure, and at a relatively low temperature e.g. 140° to 160° C. I have observed substantially no reaction at temperatures below 135° C.

Also in a preferred embodiment in accordance with the present invention, the liquid reaction mixture is stirred vigorously during the contacting. This appears to enhance the immediate vaporization of the furfuryl alcohol product. Also, the carbon monoxide gas which is formed serves as a sweep to enhance the removal of the product. If desired an additional inert gas sweep such as $N_2$ can be used.

As indicated above, either soluble homogeneous catalysts can be used or solid heterogeneous catalysts can be used. In a pair of otherwise comparable runs, except for slight variations in pressure, a soluble catalyst (palladium acetate with calcium acetate additives) gave a productivity rate of 500 grams of furfuryl alcohol per gram of metal per hour (150 mm Hg.), whereas an insoluble heterogeneous catalyst (5 percent palladium on alumina with calcium acetate) at 175 mm Hg. gave a productivity rate of 670. Insoluble forms are preferred.

The invention is further illustrated by the following examples in which all temperatures are expressed in degrees centigrade and all parts are expressed in parts by weight.

equipped as in the "batch" reaction previously mentioned above. A small amount of hydroxymethylfurfural (3 parts) was put into the flask at the start of the reaction — and a dropping funnel was used to add incrementally the rest (23.7 parts) after the reaction was initiated. An oil bath heated to 200° C. was used to heat the reaction (the oil bath was equilibrated as in previous reactions) and the reactor was evacuated to provide a pressure therein of 150 mm Hg. The rate of subsequent hydroxymethylfurfural addition was comparable to the rate of distillate produced. During the first few minutes of the reaction considerable bubbling was noted. Upon complete addition of the 23.7 parts, addition of hydroxymethylfurfural referred to above was terminated, and reaction bath temperature was maintained however until the reaction stopped, and the reactor was removed from the bath when the product ceased distilling. The product from the receiver and the trap were analyzed quantitatively by VPC, and the conversion and yields are tabulated in Table I. In Table I, DBP is di butyl phthalate, and DOP is di octyl phthalate. Also, FA refers to furfuryl alcohol and HMF refers to hydroxymethylfurfural. "Neat" means no solvent was used.

TABLE I $$OHC{-}\square{-}CH_2OH \rightarrow \square{-}CH_2OH + CO$$

| | Reaction Type | Solvent/ Conc. | Temperature | Pressure | co-Catalyst | Yield | Conv. | Selectivity to FA |
|---|---|---|---|---|---|---|---|---|
| 1-1 | Batch | DBP/10% | 165–170° C. | 100mm Hg. | $Na_2CO_3$ | VPC of trap showed FA + FA dimer as products | | |
| 1-2 | Batch | DOP/10% | 145–155° C. | 20–30mm Hg. | $Na_2CO_3$ | NMR of dry ice trap showed FA + HMF mixture | | |
| 1-3 | Batch | DBP/10% | 160° C. | 30mm Hg. | $Na_2CO_3$ | 63% | 96% | 65% |
| 1-4 | Batch | Neat | 135–140° C. | 1–2mm Hg. | $Ca(OAc)_2$ | Distilled material showed FA ~ 15–20% yield. | | |
| 1-5 | Batch | Neat | 165–180° C. | 20–30mm Hg. | $Ca(OAc)_2$ | 51% | 95% | 54% |
| 1-6 | Batch | ETOAc extract of crude HMF* | 170–180° C. | 100mm Hg. | $Ca(OAc)_2$ | 50% | >95% | — |
| 1-7 | Contin. Technique | Neat | 200° C. | 150mm Hg. | $Ca(OAc)_2$ | 60% | — | — |
| 1-8 | Contin. Technique | Neat | 200° C. | 150mm Hg. | $Ca(OAc)_2$ | 79% | 87% | 91% |
| 1-9 | Contin. Technique | Neat | 200–210° C. | 150mm Hg. | $Ca(OAc)_2$ | 69% | 90% | 77% |
| 1-10 | Contin. Technique | DBP/25% | 170–180° C | 100mm Hg. | $Ca(OAc)_2$ | 67% | >95% | >67% |

*Contains about 5% $H_2O$.

EXAMPLE 1

In Example 1 a number of contacting reactions are carried out, and the pertinent operating parameters and results are tabulated in Table I.

In Table I, in the tests which are identified as "batch", 10 parts of hydroxymethylfurfural, 1.2 parts of so-called "co-catalyst" (alkali metal or alkaline earth metal salt), 1.0 parts of 5 percent $Pd/Al_2O_3$ were also placed in a 3-neck flask equipped with a thermometer, take-off distillation head, condenser, and receiver. An oil bath heated to 135°–180° C. was used to heat the reaction (bath was equilibrated before immersing the flask) and a partial vacuum is drawn in the reactor prior to immersion in the bath. The pressures in the reactor are stated in the table. A dry ice trap was connected between the receiver and the vacuum pump, and the receiver was placed in an ice bath to keep volatile material from escaping. The product from the receiver and dry ice trap were analyzed quantitatively by VPC. The yields and conversion are reported in Table I.

In those runs identified as 1-7, 1-8; and 1-9, "continuous technique", calcium acetate 1.2 parts, and catalyst 5 percent $Pd/Al_2O_3$ 1.0 parts, were put into a 3-neck flask The run identified as 1-4 shows the relatively poor reaction achieved at temperatures in the 135°–140° C. range, probably due to resinification of HMF. Run 1-6 used a neat ethyl acetate extract of crude HMF, the feed containing 5 percent water.

EXAMPLE 2

A series of experiments were run to compare the efficacy of several catalysts. The reaction conditions are set forth at the top of Table II. The conditions and equipment employed in this series of tests are substantially identical, except for the constants stated at the top of Table II, to those referred to in the description of the "batch" procedure in Example 1. The results of the catalyst screening tests are summarized in Table II.

TABLE II
CATALYST SCREENING

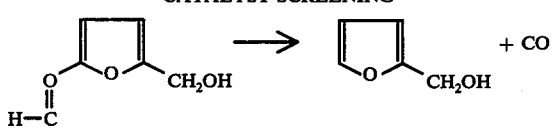

| Catalyst/ | Parts Noble | Productivity Rate | Catalyst | Parts Noble Metal Parts HMF |
|---|---|---|---|---|
| 2-1 | 5% Pd/Al$_2$O$_3$ | .025 | 672 | powder | .25% |
| 2-2 | 5% Rh/Al$_2$O$_3$ | .025 | 8 | powder | .25% |
| 2-3 | 5% Pt/Al$_2$O$_3$ | .025 | nil | powder | .25% |
| 2-4 | PtO$_2$ | .025 | nil | powder | .25% |
| 2-5 | 1% Pd/Al$_2$O$_3$ | .025 | 500 | ⅛" pellets | .25% |
| 2-6 | Pd(OAc)$_2$ 5% | .024 | 500 | soluble powder | .24% |
| 2-7 | 5% Ru/Al$_2$O$_3$ | .025 | nil | powder | .25% |
| 2-8 | Na$_2$PdCl$_4$ | .025 | 65 | soluble powder | .25% |
| 2-9 | CO$_2$(CO)$_6$(Pϕ$_3$)$_2$ | .025 | 0 | powder | .25% |
| 2-10 | Cu(OAc)$_2$ MgBr$_2$ | — | 0 | soluble crystals | — |
| 2-11 | RhCl(CO)(Pϕ$_3$)$_2$ | .048 | 54 | soluble powder | .48% |
| 2-12 | Pd(OAc)$_2$ | .025 | 98 | soluble powder | .25% |
| 2-13 | Ca(OAc)$_2$ | — | No FA Produced | | |

Constants:
Temperature 200° C.
10 parts HMF batch
.5 parts Ca(OAc)$_2$
150 mm Hg. pressure According to the data set forth in Table II, catalysts can be listed as "active" or "inactive" as summarized in the Table below:

| Active Catalysts | | | | | |
|---|---|---|---|---|---|
| Catalysts | Physical State | Type | Catalysts | Physical State | Type |
| 5% Pd/Al$_2$O$_3$ | powder | heterogeneous | PtO$_2$ | powder | heterogeneous |
| 5% Rh/Al$_2$O$_3$ | powder | heterogeneous | 5% Ru/Al$_2$O$_3$ | powder | heterogeneous |
| 1% Pd/Al$_2$O$_3$ | ⅛" pellets | heterogeneous | Co(CO)$_6$(Pϕ$_3$)$_2$ | powder | homogeneous |
| Pd(OAc)$_2$ | powder | homogeneous | Cu(OAc)$_2$/MgBr$_2$ | powder | heterogeneous |
| Na$_2$PdCl$_4$ | powder | homogeneous | | | |
| RhCl(CO)-(Pϕ$_3$)$_2$ | powder | homogeneous | | | |

Hence, rhodium and palladium were found to be useful catalysts, in accordance with the present invention, whereas platinum, ruthenium, cobalt and copper were not.

It is noted the calcium acetate by itself, was not active as a catalyst (see run 2-13).

EXAMPLE 3

The purpose of this example is to provide a further comparison of "productivity rate" studies. Some of the runs posted in Table II are restatements of runs reported in Example 2. All runs reported in Table III are at 200° C. bath temperature.

TABLE III

| | Catalyst | Co-Catalyst | Pressure | Stirring | Additional Agitation | Productivity Rate pFA/pPfd/hr. | Parts Noble Metal | Form | Parts Noble Metal / Parts HMF × 100 |
|---|---|---|---|---|---|---|---|---|---|
| 3-1 | 5% Pd/Al$_2$O$_3$ | Ca(OAc)$_2$ | 125mm Hg. | Yes. | No. | 286 | .025 | powder | .25% |
| 3-2 | 5% Pd/BaSO$_4$ | Ca(OAc)$_2$ | 155mm Hg. | Yes | No | 279 | .025 | powder | .25% |
| 3-3 | 5% Pd/Al$_2$O$_3$ | Ca(OAc)$_2$ | 175mm Hg. | Yes | Yes A | 672 | .025 | powder | .25% |
| 3-4 | 1% Pd/Al$_2$O$_3$ | Ca(OAc)$_2$ | 175mm Hg. | Yes | Yes B | 500 | .025 | pellets | .25% |
| 3-5 | Pd(OAc)$_2$ | Ca(OAc)$_2$ | 150mm Hg. | Yes | Yes A | 266 | .237 | soluble powder | 2.37% |
| 3-6 | Pd(OAc)$_2$ | Ca(OAc)$_2$ | 150mm Hg. | Yes | Yes A | 500 | .025 | soluble powder | .25% |
| 3-7 | Pd(OAc)$_2$ | None | 150mm Hg. | Yes | Yes A | 98 | .025 | soluble powder | .25% |

A 3.5g of catalyst support consisting of alumina pellets having no catalyst thereon was used. This amount was chosen because it was the same number of pellets that were used in the reactions using the pelletized Pd/Al$_2$O$_3$ catalyst to give comparable agitation in systems using powder or soluble catalyst.

Also, the invention is not limited to the liquid phase reaction conditions described above. For example, trickle bed reaction conditions with 1/16 inch pellets of 0.5 percent Pd on Al$_2$O$_3$, heated to 180°-200° C. with a N$_2$ sweep gave results comparable to those reported under "Batch" in Table I.

Also, the procedure used for determining pH of the HMF can also be used to determine the acidity or non-acidity of any contemplated materials, such as catalyst carriers.

In view of the foregoing it is manifest that the present invention provides a novel route to the manufacture of furfuryl alcohol, which route does not utilize pentosan-derived ingredients, but does utilize a hexose-derived material.

I claim:

1. The method of producing furfuryl alcohol comprising: contacting hydroxymethylfurfural with a catalyst selected from the group palladium and rhodium; continuously removing furfuryl alcohol from the contacting mixture by distillation therefrom; said contacting taking place at a temperature above 135° C., said hydroxymethylfurfural having a pH between 6.5 and 9 inclusive.

2. The method of claim 1 in which said contacting takes place in the presence of a neutral or basic salt of an alkali, or alkaline earth, metal.

3. The method of claim 1 in which said contacting takes place in the presence of sodium carbonate.

4. The method of claim 1 in which said contacting takes place in the presence of calcium acetate.

5. The method for producing furfuryl alcohol comprising: contacting hydroxymethylfurfural in the liquid phase with a catalyst selected from the group palladium and rhodium; continuously removing furfuryl alcohol from the contacting mixture by distillation therefrom; said contacting taking place at a temperature above 135° C., said hydroxymethylfurfural having a pH between 6.5 and 9 inclusive.

6. The method of claim 5 in which said contacting takes place in the presence of a neutral or basic salt of an alkali metal, or alkaline earth metal.

7. The method of claim 5 in which said contacting takes place in the presence of sodium carbonate.

8. The method of claim 5 in which said contacting takes place in the presence of calcium acetate.

* * * * *